(12) United States Patent (10) Patent No.: US 8,558,077 B2
Shellenberger (45) Date of Patent: Oct. 15, 2013

(54) EDIBLE BEAN LINE <06203> (SINALOA)

(75) Inventor: Ron Shellenberger, Kuna, ID (US)

(73) Assignee: AmeriSeed LLC, Decatur, IL (US)

( * ) Notice: Subject to any disclaimer, the term of this patent is extended or adjusted under 35 U.S.C. 154(b) by 199 days.

(21) Appl. No.: 13/210,707

(22) Filed: Aug. 16, 2011

(65) Prior Publication Data

US 2012/0054895 A1 Mar. 1, 2012

Related U.S. Application Data

(60) Provisional application No. 61/377,660, filed on Aug. 27, 2010.

(51) Int. Cl.
*A01H 5/00* (2006.01)
*A01H 5/10* (2006.01)
*A01H 4/00* (2006.01)
*C12N 15/82* (2006.01)

(52) U.S. Cl.
USPC ........... 800/313; 800/260; 800/278; 435/410; 435/430

(58) Field of Classification Search
None
See application file for complete search history.

(56) References Cited

U.S. PATENT DOCUMENTS 7,615,683 B2 * 11/2009 Webster ..................... 800/298

OTHER PUBLICATIONS

U.S., PVP Certificate for Field Bean (*Phaseolus vulgaris*), Variety 'La Paz', PVP No. 200500219, Mar. 6, 2006.

* cited by examiner

*Primary Examiner* — Stuart F Baum
(74) *Attorney, Agent, or Firm* — Andrew F. Nilles

(57) ABSTRACT

An edible bean seed designated as <06203> or Sinaloa, a sample of the edible bean deposited under accession no. PI 660004 PVPO is disclosed. Methods of using the edible bean seed designated as <06203> or Sinaloa for breeding new varieties of bean seed are also disclosed, as well as seeds of the edible bean seed designated as <06203> or Sinaloa.

15 Claims, 1 Drawing Sheet

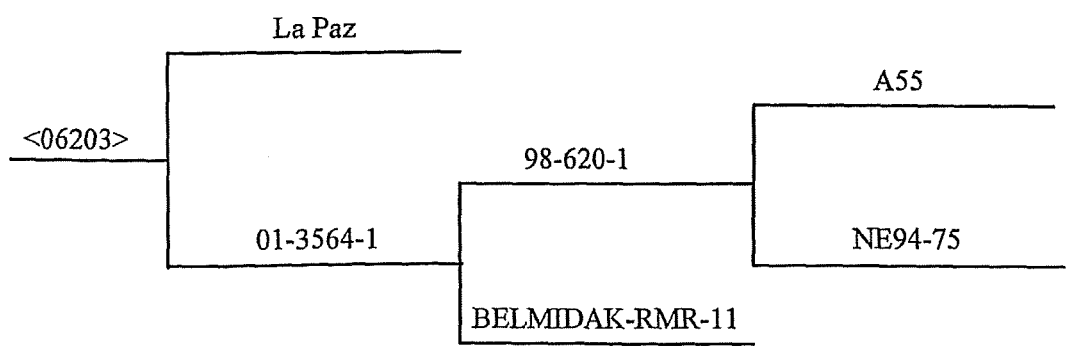

EDIBLE BEAN LINE <06203> (SINALOA)

CROSS-REFERENCE TO RELATED APPLICATIONS

This application claims the benefit under 35 U.S.C. §119 (e) of U.S. Provisional Application Ser. No. 61/377,660, filed Aug. 27, 2010, the contents of the entirety of which are incorporated by this reference.

TECHNICAL FIELD

The present invention relates generally to the field of plant breeding, and more specifically to edible bean line <06203> (Sinaloa).

BACKGROUND OF THE INVENTION

In the United States, there is increasing concern over the consumption of high sugar and high fat foods by the population. An alarming increase in obesity among the citizens in the United States exists since many people in the United States are overweight due to a lack of exercise and poor eating habits.

Beans and peas are listed under both the Vegetables, and the Meats and Beans categories of the Dietary Guidelines Pyramid, thus, emphasizing the healthy nature of legumes in the diet. In addition to the emphasis on lower fat and lower sugar diets, beneficial effects of legumes are becoming apparent. Legumes are packed with fiber and protein, as well as being a good source of numerous vitamins and minerals. Legumes also have a low glycemic index and may help play a role in maintaining normal blood sugar levels; increasing digestive health; and even possibly improving heart health. Yet, legumes are an underutilized food in the United States diet.

With the increased awareness of the problems of obesity, poor eating habits, and the increased awareness of the health benefits of legumes, there exists a need for healthier food products and foodstuffs that provide the beneficial nutritional effects of legumes, as well as a consistent crop supply of such legumes.

SUMMARY OF THE INVENTION

In each of its various embodiments, the present invention helps fulfill these needs and discloses a pinto bean variety for use in breeding new bean varieties, as well as a foodstuff.

In one embodiment, an edible bean seed designated as <06203> or Sinaloa, a sample of the edible bean deposited under accession no. PI 660004 PVPO is disclosed.

In another embodiment, methods of using the edible bean seed designated as <06203> or Sinaloa for breeding new varieties of bean seed are disclosed. Seeds of the edible bean seed designated as <06203> or Sinaloa are also disclosed.

BRIEF DESCRIPTION OF THE DRAWINGS

FIG. 1 shows the breeding history of edible bean line <06203> (Sinaloa) and its parents.

DETAILED DESCRIPTION OF THE INVENTION

In one embodiment, an edible bean line designated as <06203>, or (Sinaloa), is disclosed. As used herein, the term Sinaloa will be used to refer to edible bean variety <06203>.

Also disclosed are bean plants having the physiological and morphological characteristics of the edible bean line designated as Sinaloa. Parts of the bean plant including, without limitation, pollen, ovules, pods and cells, as well as uses of such parts in breeding are further disclosed.

In another embodiment, seed of the edible bean line designated as Sinaloa is disclosed. Such seed may be an essentially homogenous population of the edible bean line designated as Sinaloa, wherein such seed of the edible bean line designated as Sinaloa is essentially free of other seed. Accordingly, the seed of the present invention comprises at least 95% or more of seed of the edible bean line designated as Sinaloa.

In yet a further embodiment, tissue culture of regenerable cells of the edible bean line designated as Sinaloa are disclosed. Such tissue culture may be capable of expressing all of the physiological and morphological characteristics of the edible bean line designated as Sinaloa, and be capable of regenerating plants having the same genotype of plants of the edible bean line designated as Sinaloa. The tissue culture may be obtained from embryos, meristems, cotyledons, pollen, leaves, anthers, roots, root tips, pistil, flower, seed and/or stalks.

In an additional embodiment, breeding methods for producing edible bean seeds, plants and/or pods using the edible bean line designated as Sinaloa of the present invention as a parent are disclosed. Such breeding methods may be used to prepare hybrid edible bean seed or plants or inbred edible bean seed or plants, where seed ultimately produced using the edible bean line designated as Sinaloa as at least one of the parents are included within the scope of this invention.

In one embodiment, methods of crossing the edible bean line designated as Sinaloa with itself of a second plant and the seeds and plants produced by such methods are disclosed. Such methods may be used for propagating edible bean line designated as Sinaloa, or can be used to produce hybrid dry bean seeds and the plants grown therefrom.

In a further embodiment, the present invention discloses a process for producing beans comprising obtaining a plant of the edible bean line designated as Sinaloa, cultivating the plant to maturity, and collecting and/or harvesting beans from the mature plant. Such beans may be used ultimately as a foodstuff, as seed or as parent in a breeding program.

The present invention further discloses methods and compositions relating to plants, seeds and derivatives of edible bean line designated as Sinaloa. This line has an erect growth habit, is indeterminate, has guides that are medium to long, and has no ability to climb. Sinaloa is a pinto bean variety, exhibiting traits including, but not limited to, early season maturity and bean rust resistance. Observations and seed increase show that edible bean line designated as Sinaloa shows uniformity and stability, without variants.

Origin and Breeding History.

Edible bean line designated as Sinaloa exhibits improved traits including, without limitation, improved maturity. The development of edible bean line designated as Sinaloa can be summarized as follows. A cross was made between ProVita's pinto breeding line '01-3564-1' as the male parent and the Ameriseed variety 'La Paz' as the female parent. The cross was made during Spring in Year 1 in the greenhouse. Edible bean line designated as Sinaloa was derived from this cross.

The breeding history of edible bean line designated as Sinaloa is shown in FIG. 1. Pinto breeding line 01-3564-1 was a cross between ProVita pinto breeding line 98-620.1 as the female parent and BELMIDAK-RMR-11 as the male parent.

Pinto breeding line 98-620-1 was a cross between the pinto breeding line NE94-75 from the University of Nebraska as the female parent and black breeding line A55 as the male parent.

TABLE 1

The following Table indicates the selections used to produce the edible bean line designated as Sinaloa.

| Year | Location | Generation | Bulk (lbs) | Single Plant Selections |
|---|---|---|---|---|
| Summer Year 1 | Twin Falls, ID-field | F1 | <1 lb | |
| Summer Year 2 | Twin Falls, ID-field | F2 | | 8 single plant selections |
| Fall Year 2 | Kuna, ID-greenhouse | F3 | <1 lb | |
| Summer Year 3 | Twin Falls, ID-field | F4 | | 2 single plant selections |
| Fall Year 3 | Kuna, ID-greenhouse | F5 | <1 lb | |
| Spring Year 4 | Kuna, ID-greenhouse | F6 | <1 lb | |
| Summer Year 4 | Twin Falls, ID-field | F7 | | 3 single plant selections |
| Spring Year 5 | Kuna, ID-greenhouse | F8 | <1 lb | |
| Summer Year 5 | Nampa, ID-field | F9 | 16 lbs | |
| Winter Year 5 | Indio, CA-field | F10 | 150 lbs | |
| Summer Year 6 | Othello, WA-field | F11 | Commercial seed production | |

Selections were done in the F2, F4 and F7 generations as follows. In the F2 generation, there was segregation for architecture, disease resistance, maturity and seed size. Single plant selections were made for upright architecture, high pod set, yield, and early maturity. Additional criteria were for resistance to bean rust and bean virus. In the F4 generation, single plant selections were made for upright architecture, high pod set, yield, and early maturity. Additional criteria were for resistance to bean rust and bean virus. In the F7 generation, single plant selections were made for upright architecture, high pod set, yield, and early maturity. Additional criteria were for resistance to bean rust and bean virus. Such selections resulted in the new edible bean line designated as Sinaloa, which was observed to be uniform, stable and substantially free of any variants within commercially acceptable limits since the F9 generation. It is known that a small percentage of off-types may occur for a characteristic of edible bean line designated as Sinaloa during multiplication.

Physiological and Morphological Characteristics of Edible Bean Line Designated as Sinaloa.

Table 2 depicts the physiological and morphological characteristics of edible bean line designated as Sinaloa.

TABLE 2

| Characteristic | Edible bean line designated as Sinaloa |
|---|---|
| Market Class | Pinto |
| Maturity | Early (80-90 days) |
| Days from planting to harvest maturity | 90 |
| Plant Habit | |
| Type | Erect growth habit-indeterminate, guides medium to long with no ability to climb |
| Average height of mature plant | 62 cm |
| Pod position | High (lower pods not touching soil surface) |
| Adaptability to machine harvest | Adapted |
| Lodging resistance | Good |
| Leaflet morphology | |
| Leaflet | Smooth and dull |
| Shape | Ovate |
| Apex of leaflet | Acuminate |
| Base of leaflet | Obtuse |
| Flower color and days to bloom | |
| Color of standard | White |
| Color of wings | White |
| Color of keel | White |
| Days to 50% bloom | 46 |
| Pod Morphology | |
| Green color pattern | Solid |
| Mature color pattern | Striped |
| Green primary color | Green |
| Mature primary color | Yellow |
| Green color modifier | Light medium |
| Mature color modifier | Light medium |
| Green secondary color | None |
| Mature secondary color | Red |
| Green cross section shape | Pear |
| Mature cross section shape | Pear |
| Green pod curvature | Slightly curved |
| Mature pod curvature | Slightly curved |
| Green pod beak orientation | Curved downward |
| Mature pod beak orientation | Curved downward |
| Green constrictions | Slight |
| Mature constrictions | Slight |
| Average number of seeds/pod | 6.3 |
| Seed Color | Semishiny and polychrome |
| Primary color | Tan |
| Secondary color | Brown |
| Color pattern | Mottled |
| Hilar ring | Present |
| Hilar ring color | Yellow |
| Seed Shape and Weight | |
| Shape of seed taken from middle of pod | Cuboid |
| Dry seed weight in g/100 g Seeds (adjusted to 12% moisture) | 36 |
| Anthocyanin Pigmentation* | |
| Flowers | Absent |
| Leaves | Absent |
| Stems | Present |
| Petioles | Present |
| Pods | Present |
| Peduncles | Present |
| Seeds | Present |
| Nodes | Present |
| Known Disease Reaction | |
| Bean Rust (common name), *Uromyces appendiculatus* (scientific name), ur3 gene (race) | Resistant |

*The pigmentation in the plant is not always apparent. Weather and location appear to play a role in whether the pigment in the plant is expressed.

Maturity of Edible Bean Line Designated as Sinaloa.

The edible bean line designated as Sinaloa of the present invention has an early maturity. An average of four years of growing the edible bean line designated as Sinaloa in Twin Falls, Id., shows that the edible bean line designated as Sinaloa matures in an average of 90.8 days. The following data and t-test shows the data.

Table 3 depicts maturity data of edible bean line designated as Sinaloa.

|  | edible bean line designated as Sinaloa, |
|---|---|
| Year | Days for maturity |
| Year 4 | 92 |
| Year 4 | 92 |
| Year 4 | 93 |
| Year 3 | 90 |
| Year 3 | 90 |
| Year 3 | 92 |
| Year 2 | 89 |
| Year 2 | 89 |
| Year 1 | 90 |

Table 4 shows the maturity t-test for the edible bean line designated as Sinaloa.

| Mean | 90.77777778 |
|---|---|
| Variance | 2.194444444 |
| Observations | 9 |
| P(T <= t) one-tail | 0.000630183 |
| T Critical one-tail | 1.859548033 |
| P(T <= t) two-tail | 0.001260366 |
| t Critical two-tail | 2.306004133 |

Deposit Information.

A deposit of the edible bean line designated as Sinaloa of the present invention has been made with the National Center for Genetic Resources Preservation, Fort Collins, Colo. The date of deposit was Oct. 14, 2010. Upon issuance of a patent, all restrictions upon the deposit will be removed, and the deposit is intended to meet all of the requirements of 37 C.F.R. §1.801-1.809. The accession number for the deposited seeds of edible bean line designated as Sinaloa is PI 660004 PVPO. The deposit will be maintained in the depository for a period of 30 years, or 5 years after the last request, or for the enforceable life of the patent, whichever is longer, and will be replaced if necessary during such period.

The present invention has been described with reference to certain exemplary embodiments, legume products, compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiment, but rather by the appended claims as originally filed.

What is claimed is:

1. An edible bean seed designated as Sinaloa, a sample of the edible bean seed deposited under accession no PI 660004 PVPO.

2. A plant, or parts thereof, produced by growing the edible bean seed of claim 1.

3. Pollen of the plant of claim 2.

4. An edible bean plant, or parts thereof, having all of the physiological and morphological characteristics of the edible bean plant of claim 2.

5. A tissue culture of regenerable cells of the edible bean plant of claim 2.

6. The tissue culture of claim 5, wherein the cells are obtained from a plant part selected from the group consisting of leaf, pollen, embryo, meristematic cell root, root tip, anther, stomatal cell, flower, seed, stem, pod and combinations of an thereof.

7. An edible bean plant regenerated from the tissue culture of claim 6, having all of the morphological and physiological characteristics of an edible bean plant grown from an edible can seed designated as Sinaloa, a sample of the edible bean seed deposited under accession no PI 660004 PVPO.

8. A method producing an edible bean seed comprising crossing two edible bean plants and harvesting the resulting edible bean seed, wherein at least one of the two edible bean plants is the edible bean plant of claim 2.

9. A method for producing a hybyrid edible bean seed comprising crossing the edible bean plant of claim 2 with a second edible bean plant and harvesting the resulting hybrid edible bean seed.

10. A plurality of the edible bean seeds of claim 1.

11. A method of planting a field, comprising planting the plurality of the edible bean seeds of claim 10 in the field.

12. A process for producing edible beans for consumption, comprising processing the plurality of the edible bean seeds of claim 10 such dint the plurality of the edible bean seeds are suitable for consumption.

13. A method for producing an edible bean seed designated as Sinaloa-derived edible bean seed, comprising:
   crossing a plant of edible bean seed designated as Sinaloa, a sample of the seed deposited under accession number PI 660004 PVPO, with a second edible bean plant to yield progeny edible bean seed; and
   growing the progeny edible bean seed to yield Sinaloa-derived edible bean plants and allowing seed of Sinaloa-derived edible bean plants to form.

14. The method of claim 13, wherein the second edible bean plant is transgenic.

15. An edible bean designated as Sinaloa-derived edible bean plant produced by the method of claim 13.

* * * * *